United States Patent [19]

Tracy et al.

[11] Patent Number: 5,900,397
[45] Date of Patent: May 4, 1999

[54] NONYLPHENOL NONIONIC GEMINI SURFACTANTS

[75] Inventors: David James Tracy; Ruoxin Li, both of Plainsboro, N.J.

[73] Assignee: Rhodia Inc., Cranbury, N.J.

[21] Appl. No.: 08/804,707

[22] Filed: Feb. 21, 1997

[51] Int. Cl.$^6$ .................................................. C11D 3/20
[52] U.S. Cl. ......................... 510/421; 510/422; 510/505
[58] Field of Search .................................... 510/421, 422, 510/505

[56] References Cited

U.S. PATENT DOCUMENTS

| | | | |
|---|---|---|---|
| 3,919,429 | 11/1975 | Grossmann et al. | 424/358 |
| 4,592,809 | 6/1986 | Fong et al. | 204/44.2 |
| 4,892,806 | 1/1990 | Briggs et al. | |
| 4,943,664 | 7/1990 | Anderson et al. | 568/623 |
| 5,403,922 | 4/1995 | Garelli-Calvet | |
| 5,488,180 | 1/1996 | Jenkins et al. | |
| 5,493,050 | 2/1996 | Varadaraj et al. | 562/41 |
| 5,534,197 | 7/1996 | Scheibel et al. | |
| 5,585,516 | 12/1996 | Varadaraj et al. | 562/42 |
| 5,643,864 | 7/1997 | Li et al. | 510/499 |
| 5,656,586 | 8/1997 | Li et al. | 510/535 |
| 5,710,121 | 1/1998 | Tracy et al. | 510/467 |

FOREIGN PATENT DOCUMENTS

| | | | |
|---|---|---|---|
| 688781 | 12/1995 | European Pat. Off. | |
| 43 21 022 | 1/1995 | Germany | |
| 2 150 569 | 7/1985 | United Kingdom | C07C 141/18 |

OTHER PUBLICATIONS

Allouch, et.al. Nonionic Amphiphilic Compounds From Aspartic And Glutamic Acids As Structural Mimics Of Lecithins JAOCS 73; No. 1 (1996) 87–95, month unavailable.

Eastoe, et.al. Properties Of New Glucamide Surfactants Langmuir 12 (1996) 2701–2705, month unavailable.

Seguer, et.al. Nonionic Amphiphilic Compounds from Lysine as Molecular Mimics Of Lecithins JAOCS 73 No. 1 (1996) 79–85, month unavailable.

Zhang, et.al. Novel Polysaccharide Surfactants. The Effect Of Hydrophilic And Hydrophobic Chain Length On Surface Active Properties J. Colloid Interface Sci. 177 (1996) 419–426, month unavailable.

Andre–Barres, et.al. New Double Chain Surfactants Derived from Glucose and Lactose New J. Chem 19, No. 4, (1995) 345–347, month unavailable.

Briggs, et.al. Synthesis and Properties of some Novel Nonionic Polyol Surfactants J. Chem. Soc. (1995) 379–380, month unavailable.

Eastoe, et.al. Properties Of A Dichained Sugar Surfactant Langmuir 10 (1994) 4429–4433, month unavailable.

Seguer, et.al. New Nonionic Surfactants from Lysine and their Performance J. Dispersion Sci. and Tech. 15; No. 5 (1994) 591–610, month unavailable.

Latge, et.al. Synthesis of Long Chain N–Alkyllactamines from Unprotected Lactose: A New Series of Nonionic Surfactants J. Dispersion Sci. and Tech. 12; No. 3 (1991) 227–237.

Micich, et.al. Wetting Properties of Nonionics from Branched Fatty Amides JAOCS 65 No. 5 (1988) 820–825.

Hjelmeland, et.al. A New Class of Nonionic Detergents with a Gluconamide Polar Group Anal. Biochem 130 (1983) 485–490.

Emmerling, et al. Preparative Methods for the Preparation of Higher Maltoligomers and Their Coupling with Aliphatic Diramines Starch 33 (1981) 202–208.

M. Rosen: Geminis: A New Generation of Surfactants Chemtech (Mar. 1993) 30–33.

Menger, et.al. Gemini Surfactants: A New Class Of Self Assembling Molecules J. Am. Chem. Soc. 115 (1993) 10083–10090, month unavailable.

Seki, et.al. Characterization Of The Complexes Of Amphiphilic Polyanions And Double Chain Cationic Surfactants Macromolecules 25 (1992) 6540–6546, month available.

Menger, et.al. Gemini Surfactants: Synthesis and Properties J. Am. Chem. Soc. 113 (1991) 1451–1452, month unavailable.

*Primary Examiner*—Jacqueline V. Howard
*Attorney, Agent, or Firm*—Craig M. Bell

[57] ABSTRACT

Novel nonylphenol nonionic gemini surfactants are extremely effective emulsifiers for oil-in-water emulsions that provide improved detergency at even low concentration levels and are characterized by the formula:

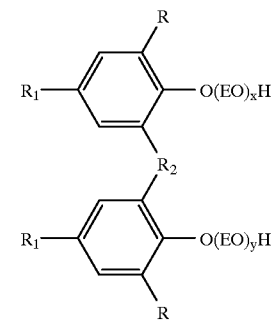

wherein R and $R_1$ are both either H or a $C_4$–$C_{22}$ alkyl, aryl, or alkylaryl with the stipulation that they cannot both be H at the same time; and $R_2$ is independently —$COR_3CO$—, —$CH_2N(R_4)CH_2$—; $CH_2N(R_5)R_6(R_5)NCH_2$—, or $R_7$—D—$R_7$ wherein $R_3$ independently represents a $C_1$–$C_6$ alkyl, branched alkyl or aryl; $R_4$ represents a $C_1$ to $C_4$ alkyl, aryl, alkylaryl, hydroxy alkyl, haloalkyl or H, $R_5$ represents a $C_1$ to $C_{10}$ alkyl or aryl and $R_6$ independently represents a $C_1$ to $C_{10}$ alkyl, aryl, or alkylaryl, $R_7$ is a $C_2$ to $C_4$ alkyl and D independently represents —S—, —SO— and $SO_2$ with the stipulation that $R_5$ and $R_6$ can form a heterocyclic ring; EO represents ethylene oxy-radicals, x and y are whole numbers and x+y equals a number from 2 to 200 inclusive.

9 Claims, No Drawings

OTHER PUBLICATIONS

Tschierske, et.al. Novel Thermotrophic And Lyotropic Double Headed Diol–Based Mesogens J. Chem. Soc. (1990) 1013–1014, month unavailable.

Fuhrhop, et.al. Routes To Functional Vesicle Membranes Without Proteins Angew. Chem. Intl. Ed. Engl. 23 (1984) 100–113, month unavailable.

Lin, I. Critical Micelle Concentration, Hydrophile Lipophile Balance, Etc. Of Ionic Surfactants Containing Two Long Chain Alkyl Groups Tenside Detergents; 17 No. 3 (1980) 113–123, month unavailable.

NONYLPHENOL NONIONIC GEMINI SURFACTANTS

This invention relates to improved surfactants useful as emulsifiers and in detergents and personal care products at very low concentrations. The surfactants also exhibit little to no toxicity which makes them useful in a wide variety of applications including personal care, cosmetics, and pharmaceuticals.

Emulsification is an extremely important technology and it is a process which is used in detergency, emulsion polymerization, cosmetics, food, agrochemicals, paints, paper, transportation of crude oil, etc. Emulsifiers function as essential ingredients in personal care and household products; industrial and institutional cleaners including hair shampoos, car washes, carpet shampoo, hand dishwashing liquids, latex foaming, oil recovery compositions; and the like.

In order to form a relatively stable emulsion, an emulsifier is required to adsorb at an oil-water interface to prevent emulsion droplet coalescence. The majority of emulsifiers are synthetic surfactants or natural products with amphiphilic character. Presently, usage levels of surfactants for effective emulsification are usually above 0.1% active based on the total weight of the detergent solution which is used in the final use composition. For a given emulsifier system, it would be advantageous to use a lower amount of surfactant to reduce the cost and amount of surfactant waste discharged into the environment; and to improve the performance of final products (e.g., the film forming and water resistance will be improved in latex paints and skin irritation will be reduced for cosmetic products).

While conventional surfactants generally have one hydrophilic group and one hydrophobic group, recently a class of compounds having at least two hydrophobic groups and at least two hydrophilic groups have been introduced. These have become known as "gemini surfactants" in the literature (*Chemtech*, March 1993, pp 30–33), and *J. American Chemical Soc.*, 115, 10083–10090, (1993) and the references cited therein). Other gemini surfactant compounds, that is, compounds having at least two hydrophilic groups and at least two hydrophobic groups are also disclosed in literature but often are not referred to expressly as gemini surfactants.

An intensive study of gemini surfactants as emulsifiers has been made. From these studies, it has been found that gemini surfactants are unexpectedly effective emulsifiers when used at very low concentrations in comparison to conventional surfactants. This finding is reflected in superior detergency at very low concentrations. Other performance properties related to emulsification as mentioned above can be also improved using low concentrations of gemini surfactants.

SUMMARY OF THE INVENTION

In accordance with the present invention, it has been discovered that gemini surfactants of the type described and claimed herein can be extremely effective emulsifiers for oil-in-water emulsions at lower concentrations than that needed utilizing corresponding conventional surfactants. Furthermore, the detergency is also improved over that provided by conventional surfactants at these low concentration levels. These novel gemini surfactants are also able to lower the monomer concentration of anionic surfactants when the two are mixed in a blend. This results in less skin irritation and the other toxic side effects of anionic surfactants.

DETAILED DESCRIPTION OF THE INVENTION

The novel surfactant compounds of the invention are based on certain gemini surfactants. As used herein, the term "gemini surfactants" is intended to mean surfactants having at least 2 hydrophobic groups and at least 2 hydrophilic groups per molecule.

A number of gemini surfactants are reported in the literature, see for example, Okahara et al., J. Japan Oil Chem. Soc. 746 (Yukagaku) (1989); Zhu et al., 67 JAOCS 7,459 (July 1990); Zhu et al., 68 JAOCS 7,539 (1991); Menger et al., J. Am. Chemical Soc. 113,1451 (1991); Masuyama et al., 41 J. Japan Chem. Soc. 4,301 (1992); Zhu et al., 69 JAOCS 1,30 (Jan. 1992); Zhu et al., 69 JAOCS 7,626 July 1992); Menger et al., 115 J. Am. Chem. Soc. 2, 10083 (1993); Rosen, Chemtech 30 (March 1993); and Gao et al., 71 JAOCS 7,771 (July 1994), all of this literature incorporated herein by reference.

U.S. Pat. No. 5,585,516 to Varadaraj et. al. discloses two tail-two head and two tail-one head surfactants including biphenolic hydrocarbon moieties. Also, gemini surfactants are briefly disclosed in U.S. Pat. No. 2,374,354, to Kaplan; U.S. Pat. Nos. 2,524,218, and 2,530,147 to Bersworth (two hydrophobic tails and three hydrophilic heads); U.S. Pat. No. 3,244,724 to Guttmann; and U.S. Pat. No. 5,160,450 to Okahara, et al., all of which are incorporated herein by reference.

The gemini surfactants of the present invention are nonylphenol, nonionic surfactants. The hydrophilic and hydrophobic groups of each surfactant moiety may be any of those known in conventional surfactants having one hydrophilic group and one hydrophobic group. For example, a typical nonionic gemini surfactant, e.g., a bis-polyoxyethylene alkyl ether, would contain two polyoxyethylene alkyl ether moieties. However, non-ionic gemini surfactants prior to this are extremely rare.

Gemini surfactants are relatively quite new and few species have been reported or disclosed in the prior art. U.S. Pat. No. 5,534,197 to Scheibel teaches a method for the preparation of a nonionic gemini surfactant wherein the hydrophilic head is a sugar or carbohydrate while the hydrophobic head is a long chain alkyl, the two joined by a short alkyl chain. U.S. Pat. Nos. 3,888,797 and 3,855,156, both to Marumo, disclose a number of nonionic gemini surfactant species in which the hydrophobic portion is comprised of a long chain lower alkyl or alkene while the hydrophilic portion is comprised of an ethoxylate group. U.S. Pat. No. 4,892,806 to Briggs and EP 0,688,781A1 to Adams also disclose sugar-based hydrophilic heads joined to the hydrophobic counterpart by a short chain carbon bridge.

Each moiety would contain a hydrophilic group, e.g., polyoxyethylene, and a hydrophobic group, e.g., an alkyl chain.

Nonionic gemini surfactants which are useful in the present invention include those of the formula:

I.

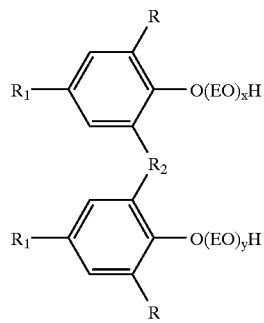

wherein both R and $R_1$ are the same and can independently be a $C_4$ to $C_{22}$ alkyl or hydrogen with the one caveat that both R and $R_1$ cannot be H; $R_2$ can independently be —$COR_3CO$—, —$CH_2N(R_4)CH_2$— and —$CH_2N(R_5)R_6(R_5)NCH_2$— or —$CH_2CH_2SO_2CH_2CH_2$— or $R_7$—D—$R_7$ wherein $R_3$ independently represents a $C_1$ to $C_6$ alkyl, branched alkyl, or aryl, $R_4$ represents a $C_1$ to $C_4$ alkyl, aryl, alkylaryl, hydroxyalkyl, haloalkyl, or H; $R_5$ represents a $C_1$ to $C_{10}$ alkyl or aryl and $R_6$ represents $C_1$ to $C_{10}$ alkyl, aryl or alkylaryl, $R_7$ is a $C_1$ to $C_4$ alkyl, D is —S—, —SO— —$SO_2$— and $R_5$ and $R_6$ can independently form a heterocyclic ring, EO represents ethyleneoxy radicals and x and y are whole number integers with the proviso that x+y is a number from 2 to 200, inclusive.

With respect to the formula comprising the compounds of the present invention, the term "alkyl" includes substituted alkyl, especially the hydroxy-substituted derivatives thereof.

Preferably, the nonionic gemini surfactants of the present invention are selected from the following structures.

II.

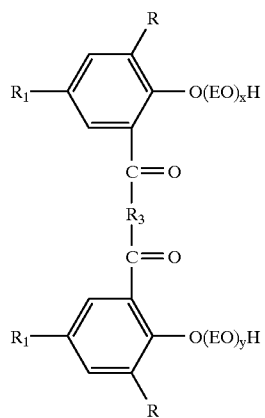

wherein R, $R_1$, and $R_3$ have been hereinbefore defined and x+y is a whole number from 2–200 inclusive.

III.

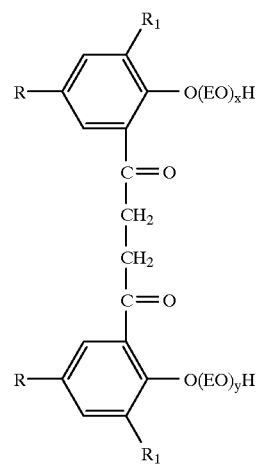

wherein R and $R_1$ have been hereinbefore defined and x+y is a whole number from 2–200 inclusive.

IV.

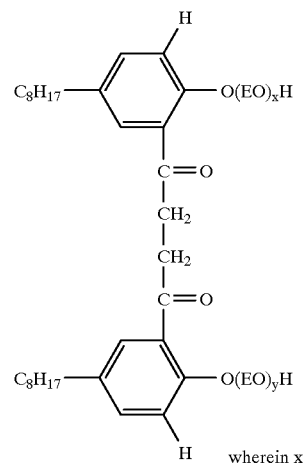

wherein x + y = 20

V. 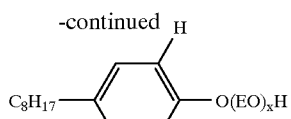

VI. 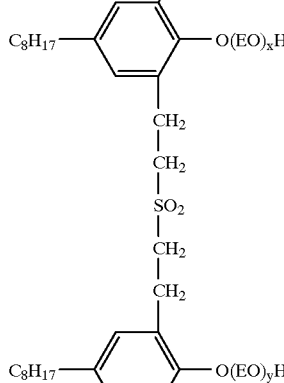

wherein x and y are whole numbers and x+y=2–200 inclusive.

The compounds of the present invention can be made by the Lewis-Acid catalyzed addition of a dicarboxylic acid or acid chloride to an alkylphenol. For example, the addition of succinic acid chloride to nonylphenol may be represented by the following reaction.

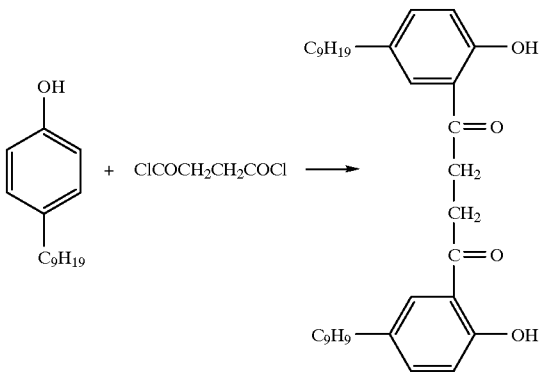

Other diacids which would be employed comprise terephthalic acid, maleic acid, malonic acid, fumaric, succinic, glutaric, itaconic 2,2-dimethylglutaric, 2,4-dimethylglutaric, pimelic, cyclohexanedicarboxylic, and adipic acid.

Mannich reactions are those in which an active methylene compound is reacted with formaldehyde and ammonia or primary and secondary amines to yield β-amino-carbonyl compounds. Mannich reactions can be used to prepare amine-coupled products. An example would be the reaction of N, $N^1$ dimethylethylene diamine and formaldehyde with nonylphenol.

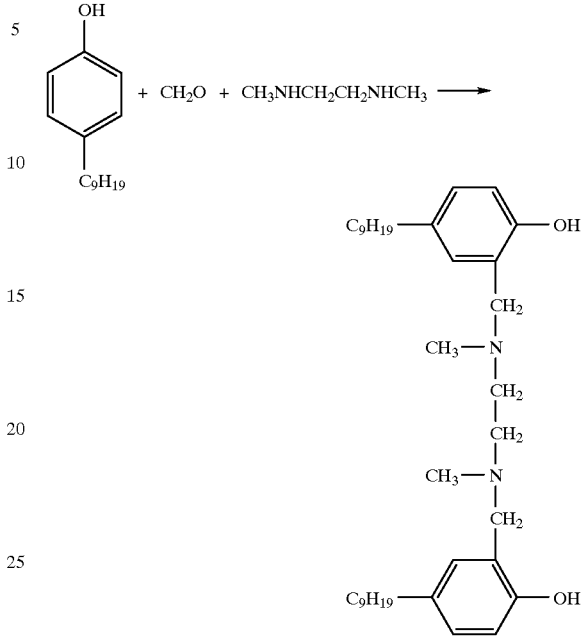

Typical amines useful in the reaction include N, $N^1$-dimethyl-1, 6-hexanediamine, methylamine, N,$N^1$-dimethyl-1,3-propanediamine, ethylamine, propylamine, butylamine, piperazine, β-hydroxyethylamine, β-chloroethylamine, benzylamine, β-phenylethylamine and mixtures thereof.

This class of gemini surfactants as disclosed in the present invention can be used in providing improved emulsions which are operable at lower concentrations than the known surfactants of the prior art.

Typical useful phenolics are ρ-octylphenol, ρ-nonylphenol, ρ-dodecylphenol, ρ-(1,1,3,3-tetramethylbutyl)phenol, ρ-2,4-diamylphenol, 2,4-di(1,1,3,3-tetramethylbutyl) phenol, 2,4,-ditertbutylphenol, 2-methyl4-octylphenol, 2-methyl-4-nonylphenol, 2-t-butyl-4-nonylphenol, 2-acetyl-4-nonylphenol, 2-acetyl, 6-methyl-4-nonylphenol and mixtures thereof.

Where desired, the surfactants used in the present invention can be oxyalkylated by reacting the product with an alkylene oxide according to known methods, preferably in the presence of an alkaline catalyst.

For alkylation conditions and commonly used alkylating agents, see Amphoteric Surfactants Vol. 12, Ed. B. R. Bluestein and C. L. Hilton, *Surfactant Science Series* 1982, pg. 17 and references cited therein, the disclosures of which are incorporated herein by reference.

The surfactant compositions comprising the gemini nonionic compounds of the invention are extremely effective in aqueous solution at low concentrations as defined herein. The surfactants of the invention can be used in any amount needed for a particular application which can be easily determined by a skilled artisan without undue experimentation.

While the gemini surfactants of the invention can be used alone, it has been unexpectedly found that blends of the compounds of the invention with certain other conventional well known anionic, nonionic, cationic and amphoteric surfactants as well as polymers and enzymes provide synergistic effects in relation to critical micelle concentration (cmc) and surface tension reducing ability, and hence improved detergency.

Another important unexpected property of the Gemini Surfactants is their ability to significantly lower the ionic monomer concentration in mixtures of anionic/nonionic or anionic/nonionic/amphoteric or anionic/nonionic/cationic surfactant mixtures. It is well know that anionic monomers that are useful in personal care systems are responsible for higher toxicity and skin irritancy. Further, anionic surfactant monomers are responsible for the deactivation of enzymes used in detergent systems and moreover, being anionic, they interact strongly with proteins and enzymes thereby deactivating them. Also anionic surfactants very often absorb onto polymers used in detergents, wastewater treatment systems and conditioning agents used in personal care applications and so on, thereby changing the charged nature of such polymers. This results in the complete loss or poor performance for the polymers in their application.

The use of gemini surfactants in very small amounts in the presence of an anionic surfactant such as lauryl ether sulfate (ESY) dramatically reduces the anionic monomers. With the addition of less than a 0.1 mole fraction of the gemini surfactant, the anionic concentration in the mixture is brought down by greater than an order of magnitude of ten. This dramatic reduction of the anionic monomer at these very low concentrations will result in the elimination of any detrimental effects discussed above and brought about as a result of the anionic monomers. Therefore, this ability to decrease the anionic (or cationic) monomers in solution should provide performance enhancement for the surfactant or the surfactant polymer/enzyme mixtures and the other performance additives very often found in detergents, and personal care formulations.

The following examples are provided to more fully disclose, describe and set forth the elements and embodiments of the surfactants of the present invention. They are for illustrative purposes only, and it is recognized that minor changes or alterations may be made to the reaction parameters, reactants and isolation procedures that are not disclosed herein. However, to the extent that any such changes do not materially alter the final product or result, such alternative measures are deemed as falling within the spirit and scope of the invention as recited by the claims that follow.

A. Preparation of Octylphenol Gemini Structure IV

IV.

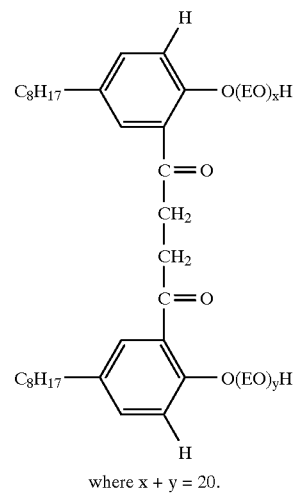

where $x + y = 20$.

EXAMPLE 1

Coupling

Aluminum chloride anhydrous, 30 g (0.2M), was added to 41.2 g (0.2 M) 4(1,1,3,3-tetramethylbutyl) phenol in 100 ml nitrobenzene at 5–10° C. over a one hour period. A solution of succinyl chloride (15.6 g, 0.1 mole) in 50 ml nitrobenzene was added over a 30 minute period and the reaction was allowed to warm to room temperature and stirred overnight. The reaction yielded 22.0 g of product.

EXAMPLE 2

Ethoxylate Preparation

Fifty (50) grams (0.1M) of the product of Example 1 was charged in an autoclave and to this was added 0.05 g potassium hydroxide flakes. The autoclave was heated to 120° C. with a nitrogen sparge to remove water. The reactor was degassed by evacuating to 20" vacuum and releasing with nitrogen. After three cycles ethylene oxide was added (89 g., 2.0 M) at a temperature of 160° C. and 60 psig. After addition was complete the reaction was cooled to 120° C., sparged with nitrogen and neutralized with acetic acid.

The residual product whose structure is set forth below as structure IV exhibited excellent surface activity as measured by surface tension measurement techniques.

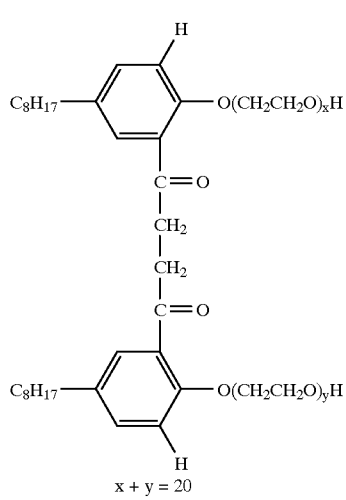

x + y = 20

B. Preparation of Methylaminomethylenebis (4,6-Diamylphenol) Intermediate A

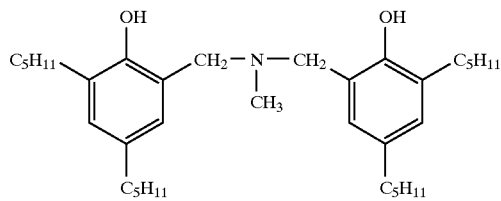

EXAMPLE 3

2,4-diamylphenol (468 gm., 2.0M) was added to one mole of methylamine (40% in water) followed by two moles of formaldehyde (as formalin). The temperature was kept at 25° to 35° C. during the addition. The reaction was stirred overnight. The organic and aqueous phases were separated and the organic phase yielded the bisphenolic compound (Intermediate A) whose composition appeared as a yellow oil.

EXAMPLE 4

Preparation of the Ethyoxylate of Intermediate A

To an autoclave was charged one mole of the intermediate bisphenolic A together with 5 g of potassium hydroxide flakes. The autoclave was heated to 140° C. and purged with nitrogen to remove water. The reactor was heated to 160° C. and ethylene oxide added to a pressure of 60 psig until 20 moles had reacted. The reactor was cooled to 120° C., the product neturalized with acetic acid and discharged. The compounds' NMR analysis spectrum agreed with the predicted structure. The product foamed when added to water and exhibited superior surface activity when measured by standard surface tension measurement techniques.

EXAMPLE 5

Preparation of Sulfone

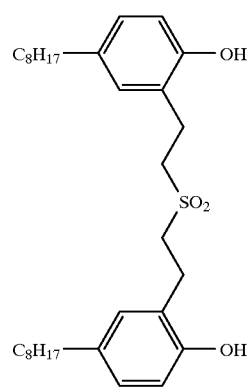

4(1,1,3,3-tetramethylbutyl)phenol (87 g, 0.42 mol) and vinyl sulfone (10 g, 0.086 M) were dissolved in 100 ml dry xylene at room temperature. The reaction solution was refluxed for 8 hours in the presence of trace pure acetic acid as catalyst. The reaction was then stopped by stripping out all the solvent and excess starting material under vacuum. The final product was collected after cooling. The reaction yielded about 40 g of product.

EXAMPLE 6

Ethoxylation of Example 5

To an autoclave was charged 53 g (0.1 mole) of the product of Example 5 and 0.1 g of potassium hydroxide flakes were added. The autoclave was heated to 120° C. with a nitrogen sparge to remove water. After degassing, ethylene oxide (3.0 mole, 132 g) was added at 150° C. to 160° C. and 40 psig. After uptake was complete, the reaction was cooled to 110° C. and neutralized with glacial acetic acid. The residue exhibited surface activity as evidenced by surface tension reduction and foaming characteristics.

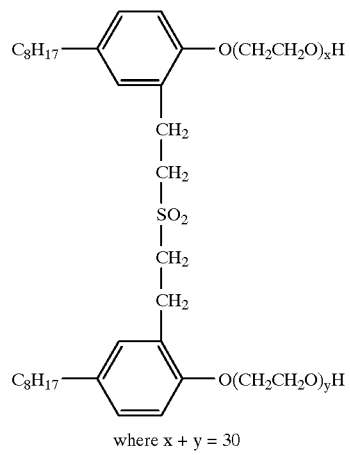

where x + y = 30

What we claim is:

1. A surfactant composition comprising one or more of the compounds comprised of the formula:

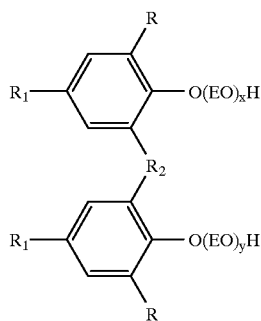

wherein R and $R_1$ are both either H or a $C_4$–$C_{22}$ alkyl, aryl, or alkylaryl with the stipulation that they cannot both be H at the same time; and $R_2$ is independently —$COR_3CO$—, wherein $R_3$ independently represents a $C_1$–$C_6$ alkyl, branched alkyl or aryl; EO represents ethylene oxy-radicals, x and y are whole numbers and x=y equals a number from 2 to 200 inclusive.

2. The composition of claim 1 further characterized by the structure:

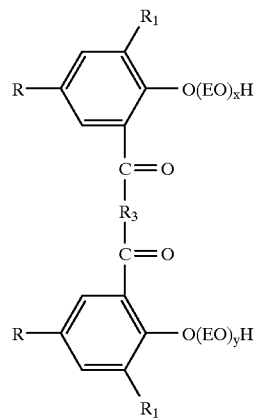

wherein R and $R_1$ have been hereinbefore defined and $R_3$ independently represents a $C_1$–$C_6$ alkyl, branched alkyl, or aryl and x and y are whole numbers and x+y equals a number from 2–200 inclusive.

3. The composition of claim 2 further characterized by the structure:

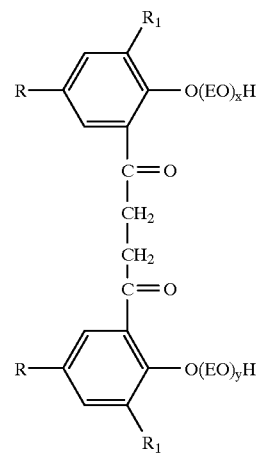

where R and $R_1$ have been hereinbefore defined and x and y are whole numbers and x+y equals a number from 2–200 inclusive.

4. The composition of claim 3 further characterized by the structure:

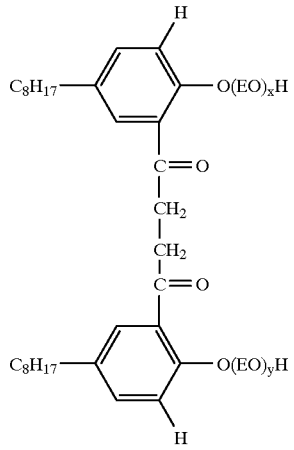

wherein x + y are whole wherein x+y are whole numbers and x+y=20.

5. A surfactant blend comprising the compound of claim 1 and one or more additional compounds selected from the group consisting of anionic surfactants, nonionic surfactants, cationic surfactants, amphoteric surfactants, and mixtures thereof.

6. A surfactant blend comprising the compound of claim 2 and one or more additional compounds selected from the group consisting of anionic surfactants, nonionic surfactants, cationic surfactants, amphoteric surfactants, and mixtures thereof.

7. A surfactant blend comprising the compound of claim 3 and one or more additional compounds selected from the group consisting of anionic surfactants, nonionic surfactants, cationic surfactants, amphoteric surfactants, and mixtures thereof.

8. The surfactant composition of claim 1 useful as an emulsifier in detergents, paints, cosmetics, foods, shampoos, oil recovery compositions, dishwashing liquids, and latex foaming compositions.

9. The surfactant composition of claim 3 useful as an emulsifier in detergents, paints, cosmetics, foods, shampoos, oil recovery compositions, dishwashing liquids, and latex foaming compositions.

* * * * *